(12) United States Patent
Grass et al.

(10) Patent No.: US 11,744,532 B2
(45) Date of Patent: Sep. 5, 2023

(54) SYSTEM FOR PROVIDING A SPECTRAL IMAGE

(71) Applicant: KONINKLIJKE PHILIPS N.V., Eindhoven (NL)

(72) Inventors: Michael Grass, Buchholz in der Nordheide (DE); Roland Proksa, Neu Wulmstorf (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 238 days.

(21) Appl. No.: 17/282,027

(22) PCT Filed: Sep. 27, 2019

(86) PCT No.: PCT/EP2019/076287
§ 371 (c)(1),
(2) Date: Apr. 1, 2021

(87) PCT Pub. No.: WO2020/070023
PCT Pub. Date: Apr. 9, 2020

(65) Prior Publication Data
US 2021/0338182 A1    Nov. 4, 2021

(30) Foreign Application Priority Data
Oct. 4, 2018 (EP) .................................. 18198673

(51) Int. Cl.
*A61B 6/00* (2006.01)
*A61B 6/03* (2006.01)
(Continued)

(52) U.S. Cl.
CPC ............ *A61B 6/4241* (2013.01); *A61B 6/025* (2013.01); *A61B 6/027* (2013.01); *A61B 6/032* (2013.01);
(Continued)

(58) Field of Classification Search
CPC ....... A61B 6/4241; A61B 6/025; A61B 6/027; A61B 6/032; A61B 6/4035; A61B 6/488;
(Continued)

(56) References Cited

U.S. PATENT DOCUMENTS 6,950,493 B2   9/2005   Besson
7,031,425 B2   4/2006   Hsieh
(Continued)

FOREIGN PATENT DOCUMENTS

JP   2009279289 A    12/2009
WO   WO2018050572 A1   3/2018

OTHER PUBLICATIONS

PCT International Search Report, International application No. PCT/EP2019/076287, dated Dec. 13, 2019.
(Continued)

*Primary Examiner* — Courtney D Thomas
(74) *Attorney, Agent, or Firm* — Larry Liberchuk

(57) ABSTRACT

The invention refers to a system for providing a spectral image using a conventional CT system. The system comprises a data providing unit (11) for providing first projection data and second projection data, wherein the first and second projection data have been acquired using different acquisition spectra, wherein the first projection data has been acquired during a scout scan and the second projection data has been acquired during a diagnostic scan, or wherein the first and second projection data have been acquired by a first and second part of the detector, respectively. The first and second part of the detector acquire projection data with different acquisition spectra. A spectral image generation unit (12) generates a spectral image based on the projection data. With this system a spectral image can be provided using a conventional CT system with a decreased acquisition time.

13 Claims, 7 Drawing Sheets

(51) Int. Cl.
*G01N 23/046* (2018.01)
*G06T 11/00* (2006.01)
*A61B 6/02* (2006.01)
*G06T 7/10* (2017.01)
*G06T 7/30* (2017.01)

(52) U.S. Cl.
CPC ......... *A61B 6/4035* (2013.01); *G01N 23/046* (2013.01); *G06T 7/10* (2017.01); *G06T 7/30* (2017.01); *G06T 11/003* (2013.01); *G01N 2223/423* (2013.01); *G06T 2207/10081* (2013.01)

(58) Field of Classification Search
CPC ...... A61B 6/482; A61B 6/405; G01N 23/046; G01N 2223/423; G06T 7/10; G06T 7/30; G06T 11/003; G06T 2207/10081; G06T 11/008
See application file for complete search history.

(56) References Cited

U.S. PATENT DOCUMENTS

| | | | |
|---|---|---|---|
| 2004/0076257 A1 | 4/2004 | McDaniel | |
| 2006/0133562 A1 | 6/2006 | Heuscher | |
| 2011/0150175 A1 | 6/2011 | Hseih | |
| 2011/0211664 A1 | 9/2011 | Brown | |
| 2013/0284939 A1 | 10/2013 | DeMan | |
| 2013/0329851 A1* | 12/2013 | Rossl | A61B 6/032 378/5 |
| 2016/0113613 A1 | 4/2016 | Ji | |
| 2017/0258412 A1 | 9/2017 | Daerr | |
| 2019/0117177 A1* | 4/2019 | Cuadros | A61B 6/03 |

OTHER PUBLICATIONS

Alvarez R.E. et al., "Energy-Selective Reconstruction X-Ray Computerized Tomography", Physics in Medicine and Biology, vol. 21, No. 5, pp. 733-744 (1976).

Maab C. et al., "Image-Based Dual Energy CT Using Optimized Precorrection Functions: A Practical New Approach of Material Decomposition in Image Domain", Medical Physics, vol. 38, No. 8, pp. 3818-3829 (2009).

Rudin L.I. et al., "Nonlinear Total Variation Based Noise Removal Algorithms", Physica D, vol. 60, Issues 1-4, pp. 259-268, Nov. 1992.

Kabus S. et al., "Evaluation of 4D-CT Lung Registration", MICCAI 2009. Lecture Notes in Computer Science, vol. 5761, pp. 747-754 (2009).

* cited by examiner

SYSTEM FOR PROVIDING A SPECTRAL IMAGE

FIELD OF THE INVENTION

The invention relates to a system, a method and a computer program for providing a spectral image.

BACKGROUND OF THE INVENTION

Generally, spectral images are generated by using a spectral CT system, for instance, a dual energy CT system. But, such a specialized spectral CT system is still not widely available today. Accordingly, it would be advantageous to provide a system that allows for spectral imaging using a conventional CT system.

SUMMARY OF THE INVENTION

It is an object of the present invention to provide a system, a method and a computer program that allow for providing a spectral image using a conventional CT system.

In a first aspect of the present invention, a system for providing a spectral image is presented, wherein the system comprises a data providing unit for providing projection data comprising first projection data and second projection data acquired using a CT system comprising a detector, wherein the first projection data has been acquired using a first acquisition spectrum and the second projection data has been acquired using a second acquisition spectrum, wherein the first projection data has been acquired during a scout scan and the second projection data has been acquired during a diagnostic scan or wherein the first projection data has been acquired by a first part of the detector and the second projection data has been acquired by a second part of the detector, wherein the first part and the second part of the detector acquire projection data with the first acquisition spectrum and the second acquisition spectrum, respectively, due to an anode heel effect, and a spectral image generation unit for generating a spectral image based on the provided projection data.

Since the data providing unit provides first projection data and second projection data, wherein the first projection data has been acquired during a scout scan using a first acquisition spectrum and the second projection data has been acquired during a diagnostic scan using a second acquisition spectrum, or since the first projection data is acquired by the first part of the detector and the second projection data is acquired by the second part of the detector, wherein the first and the second part of the detector acquire projection data with a first acquisition spectrum and a second acquisition spectrum, respectively, due to the anode heel effect, it becomes possible to acquire projection data comprising different spectral information with a conventional CT system. Accordingly, from the spectral information of the first and second projection data a spectral image can be generated, such that the system allows to generate a spectral image with a conventional CT system. Moreover, the first projection data and the second projection data can be acquired either during the same scan by using the first and the second part of the detector or the first projection data can be acquired very fast during a scout scan, for instance, with a lower resolution than the second projection data, such that the time for acquiring the first and the second projection data and thus for acquiring the information necessary for providing a spectral image using a conventional CT system can be decreased. Thus, a spectral image can be provided using a conventional CT system with a decreased acquisition time.

The data providing unit is adapted to provide projection data that has been acquired during a CT scan of an object. The data providing unit can be, for instance, directly connected to the CT system used for acquiring the projection data and directly provide the projection data acquired by the CT system. Moreover, the data providing unit can also be a part of the CT system acquiring the projection data. Alternatively, the data providing unit can be separate from the CT system and/or can be connected, for instance, to a storage unit storing projection data of the object that has been acquired by the CT system. Further, the data providing unit can itself be configured as a storage unit storing the projection data of the object. The object can be any object scanned by the CT system, for instance, a human being, an animal or an inanimate object, like a suitcase. In a preferred embodiment, the object is a patient and the CT system is a conventional medical CT system, wherein a conventional medical CT system refers to a non-spectral CT system, i.e. a CT system not specifically constructed to provide spectral images. In particular, the CT system can be a CT system comprising conventional detector elements, i.e. non-spectral detector elements, wherein the projection data from the conventional detector elements are used for generating the spectral image. Thus, the CT system can also be a CT system comprising a hybrid detector. A hybrid detector comprises both spectral detector elements, i.e. detector elements allowing energy discrimination of the incoming radiation, and conventional detector elements, i.e. detector elements integrating the energy of the received radiation. The different detector elements of a hybrid detector can be arranged in different ways, for instance, such that the first and last rows of the detector comprise conventional detectors and the middle rows of the detector comprise spectral detector elements, or vice versa. The spectral detector elements can also be provided in the middle of the detector and be surrounded by the conventional detector elements, or vice versa. The different detector elements can also be arranged in a checkerboard fashion. They may also be arranged in a way that the spectral detectors cover an area along the fan direction of the detector while the remaining part of the detector is filled with conventional detector elements. Other types of mixing detector elements are also imaginable. In such an embodiment the invention allows to use not only the projection data acquired with the spectral detector elements for reconstructing a spectral image, but also the projection data from the conventional detector elements.

The projection data provided by the data providing unit comprises first projection data and second projection data, wherein the first projection data has been acquired using a first acquisition spectrum and the second projection data has been acquired using a second acquisition spectrum. The acquisition spectrum refers to the spectrum of the radiation, i.e. x-ray radiation, provided by a radiation source, i.e. an x-ray radiation source, of the CT system. Accordingly, the first projection data provided by the data providing unit has been acquired with radiation comprising the first acquisition spectrum and the second projection data has been acquired with radiation comprising the second acquisition spectrum. The first acquisition spectrum and the second acquisition spectrum are different from each other, i.e. comprise different spectral characteristics.

In an embodiment, the data providing unit is adapted to provide first projection data that has been acquired during a scout scan and second projection data that has been acquired during a diagnostic scan. A scout scan refers to a scan of the object that is acquired before the diagnostic scan. Generally, a scout scan is acquired in a very fast way and with a signal-to-noise ratio being lower than the signal-to-noise ratio of a diagnostic image. A scout scan can be used for planning the diagnostic scan, for instance, for determining a region of interest in a scout image reconstructed based on the projection data from the scout scan, wherein the diagnostic scan is then confined to the region of interest determined in the scout image. Also other functions of a scout scan can be contemplated, for instance, determining the position of a patient, radiation dose calculations for the radiation dose to be provided to the object during the diagnostic scan, determining or optimizing imaging settings for the diagnostic scan, etc. A diagnostic scan refers to a scan of the object with imaging settings that allow providing a diagnosis of the object based on diagnostic images reconstructed from the projection data acquired during the diagnostic scan. These imaging settings can refer, for instance, to a good signal-to-noise ratio, a high resolution, a high contrast between certain structures of the object, etc.

In an embodiment, the data providing unit is adapted to provide first projection data that has been acquired by a first part of the detector of the CT system and second projection data that has been acquired by a second part of the detector of the CT system. The first projection data acquired by the first part of the detector has been acquired with a first acquisition spectrum and the second projection data acquired by the second part of the detector has been acquired with a second acquisition spectrum due to the anode heel effect. The anode heel effect leads to a variation of intensity of radiation, i.e. x-ray radiation, emitted by an anode of a radiation source, wherein the variation of the radiation intensity depends on the direction of the emission of the radiation. Accordingly, different parts of a detector detecting the radiation emitted by the radiation source experience radiation with different radiation spectra. Thus, due to the anode heel effect, different parts of the detector acquire projection data with different acquisition spectra. In a preferred embodiment the first projection data acquired with the first part of the detector and the second projection data acquired with the second part of the detector have been acquired using a spectral filter that increases a spectral difference of the first acquisition spectrum and the second acquisition spectrum caused by the anode heel effect.

In this embodiment, the first projection data is acquired using a first part of the detector and the second projection data is acquired using a second part of the detector. The first and the second part of the detector are defined by being irradiated with different acquisition spectra. Accordingly, the first and the second part of the detector are defined by the position and spectral radiation characteristic of an anode of a radiation source of the CT system. The first part and the second part of the detector can refer to any part of the detector that allows the acquisition of projection data with different acquisition spectra due to the anode heel effect. For instance, the first part of the detector can refer to a first half of the detector and the second part of the detector can refer to a second half of the detector in a direction providing different acquisition spectra due to the anode heel effect, wherein the first and the second part do not overlap. Alternatively, the first part of the detector and the second part of the detector can comprise an overlapping region, in which the first part of the detector and the second part of the detector overlap. Also, the first part of the detector and the second part of the detector together can refer to only a fraction of the detector, i.e. the first part and the second part together can be smaller than the whole detector. For instance, the first part of the detector can refer to a first third of the detector and the second part of the detector can refer to a second third of the detector, wherein one third of the detector might not be used for acquiring projection data. Further, if the detector comprises detector elements, wherein the detector elements form detector element rows, the first and the second part can be defined by the detector element rows. For instance, the first part can refer to the first three detector rows and the second part can refer to the last three detector rows in a direction defined by providing a difference between the acquisition spectra.

Moreover, the data providing unit is preferably adapted to provide third projection data having been acquired using a third acquisition spectrum at a third part of the detector, wherein also the third part of the detector acquires projection data with a third acquisition spectrum due to the anode heel effect. In this preferred embodiment, the spectral image generating unit is adapted to generate the spectral image based on the provided projection data comprising the first, second and third projection data. Furthermore, the data providing unit can be adapted to provide further projection data, for instance, fourth projection data, in addition to the first, the second and the third projection data. Thus, the data providing unit can provide any number of further projection data in addition to the first and second projection data, wherein each further projection data would be acquired with a further acquisition spectrum using a further part of the detector, wherein all acquisition spectra comprise different spectral characteristics. Also for all further projection data the corresponding parts of the detector can comprise an overlapping region with any of the other parts of the detector. The spectral image generation unit is in this case adapted to generate the spectral image also based on the further projection data.

The spectral image generation unit is adapted to generate the spectral image based on the provided projection data comprising the first projection data and the second projection data. In particular, the spectral image generation unit is adapted to generate the spectral image based on the first projection data and the second projection data, for instance, based on differences between the first projection data and the second projection data caused by the different acquisition spectra and providing spectral information of the imaged object. Since the first projection data and the second projection data have been acquired with a first acquisition spectrum and a second acquisition spectrum, spectral information of the imaged object is available for generating the spectral image. The spectral image can be, for instance, a material image, a content scatter image, a K-edge image, a mono-energetic image, etc. Moreover, the spectral image generation unit can be adapted to generate more than one spectral image based on the provided projection data, for instance, to generate an image showing a first material of the object and an image showing a second material of the object. An exemplary method for generating a spectral image is described, for instance, in the article "Energy-selective Reconstruction X-ray Computerized Tomography" by R. Alvarez et al, Physics in Medicin and Biology, volume 21, pages 733-744 (1976).

In an embodiment, the CT system comprises a radiation source and the first projection data acquired during a scout scan has been acquired by operating the radiation source with a first radiation energy and/or by providing the radiation source with a first filter for filtering the radiation of the radiation source and the second projection data acquired during the diagnostic scan has been acquired by operating the radiation source with a second radiation energy and/or by providing the radiation source with a second filter for filtering the radiation of the radiation source. If the radiation source is operated with the first radiation energy, i.e. with a first voltage, the radiation emitted by the radiation source will comprise a first acquisition spectrum, i.e. a first spectral characteristic, and when the radiation source is operated with the second radiation energy, i.e. a second voltage, the radiation emitted by the radiation source will comprise a second acquisition spectrum, i.e. a second spectral characteristic. Preferably, the first radiation energy can lie within a range between 70 and 90 keV, and the second radiation energy can lie within a range between 120 and 140 keV. Alternatively, the second radiation energy can lie within a range between 70 and 90 keV, and the first radiation energy can lie within a range between 120 and 140 keV. Moreover, if the radiation source is provided with a first filter for filtering the radiation emitted by the radiation source, the emitted radiation detected by the detector will comprise a first acquisition spectrum, and if the radiation source is provided with the second filter for filtering the radiation emitted by the radiation source, the radiation detected by the detector will comprise a second acquisition spectrum. Preferably the first and the second filer can comprise a tin potential filter.

In an embodiment, the scout scan has been acquired with a tube current being lower than the tube current at which the diagnostic image has been acquired and/or wherein the scout scan has been acquired with a spatial resolution being lower than the spatial resolution with which the diagnostic image has been acquired. The spatial resolution of projection data refers to the amount of information, i.e. the amount of projection values, per spatial volume that are acquired during the scanning of an object, i.e. during the acquisition of the projection data. The spatial resolution of the projection data depends, for instance, on the radiation energy with which the projection data is acquired, on the relative movement of the detector with respect to the object during the acquisition, etc. If the projection data is acquired in a helical scan mode, the spatial resolution further depends on a pitch with which the projection data is acquired. Moreover, the spatial resolution can also be changed by adapting, for instance, the number of projections acquired, the size of the focal spot, the size of the detector elements by connecting or disconnecting detector elements with each other, etc. If the first spatial resolution is lower than the second spatial resolution, the first projection data can be acquired much faster than the second projection data. In a preferred embodiment, the first projection data acquired with the first resolution corresponds to projection data that has been acquired during a 3D scout scan. In other embodiments the scout scan can also be a 2D scout scan. Moreover, the first projection data can also be acquired during two 2D scout scans. It is necessary in many medical applications to acquire first a scout scan that allows to exactly determine the region of interest that should be imaged during a following diagnostic CT scan. Accordingly, if the scout scan is acquired using a first acquisition spectrum, for instance, by operating the radiation source with a first energy, and the follow-up scan, i.e. diagnostic scan, is acquired using a second acquisition spectrum, for instance, by operating the radiation source with a second energy, first and second projection data, respectively, can be provided without requiring additional acquisition time or exposing a patient to additional radiation.

In an embodiment, the data providing unit is further adapted to provide spectral characteristics indicative of the characteristics of the first acquisition spectrum and of the second acquisition spectrum, wherein the spectral generation unit is adapted to generate the at least one spectral image based further on the provided spectral characteristics. Preferably, the data providing unit is adapted to provide spectral characteristics that have been measured during a calibration measurement using the CT system and settings of the CT system that are used for acquiring the projection data. Alternatively, the data providing unit can be adapted to provide spectral characteristics that have been modelled using a model of the CT system, in particular of the radiation source of the CT system. If the data providing unit provides the first projection data that has been acquired during a scout scan and the second projection data that has been acquired during a diagnostic scan, the data providing unit is further adapted to provide the spectral characteristics indicative of the first spectrum that have been measured or modelled for the CT system using the settings of the CT system used for acquiring the first projection data and the spectral characteristics indicative for the second spectrum measured or modelled for the CT system using the settings used for acquiring the second projection data. If the data providing unit provides the first projection data acquired with the first part of the detector and the second projection data acquired with the second part of the detector, the data providing unit is further adapted to provide the spectral characteristics indicative of the characteristics of the first spectrum by measuring or modelling characteristics of the spectrum of the radiation received by the first part of the detector and to provide the spectral characteristics indicative of the characteristics of the second acquisition spectrum that has been acquired by measuring or modelling the radiation received by the second part of the detector. An exemplary method using the spectral characteristics for generating a spectral image is described, for instance, also in the article "Energy-selective Reconstruction X-ray Computerized Tomography" by R. Alvarez et al, Physics in Medicin and Biology, volume 21, pages 733-744 (1976).

In an embodiment, the first projection data acquired with the first part of the detector and the second projection data acquired with the second part of the detector have been acquired during a same acquisition scan, wherein the acquisition scan has been performed in a helical scan mode with a pitch smaller than 1. The pitch of a CT system in a helical scan mode is defined as a table distance travelled in one 360° gantry rotation divided by the detector height, wherein the detector height is defined as a height of the detector projected on the rotation axis. Accordingly, a pitch being smaller than 1 refers to a scan mode in which a region of the object imaged during consecutive 360° gantry rotations partly overlaps. For instance, during an exemplary first 360° gantry rotation, a region of the object is imaged by the first part of the detector, wherein in an exemplary subsequent second 360° gantry rotation the same region of the patient is imaged by the second part of the detector. The pitch preferably used for acquiring the provided projection data depends on the extent of the first and/or second part of the detector in an acquisition scan direction. In a helical scan mode, the acquisition scan direction is defined as a direction opposite to a direction in which the table travels, i.e. as a direction parallel to a table in which the helical trajectory of the radiation source extends. Moreover, in this preferred embodiment, the first part of the detector refers to a part of the detector being, in acquisition scan direction, in front of a part of the detector to which the second part of the detector refers. More preferably, in this embodiment, the pitch is selected such that the first part of the detector, during a 360° gantry rotation, images a same region of the object as the second part of the detector during a subsequent 360° gantry rotation. Moreover, if the data providing unit is adapted to provide third projection data, the data projection unit is adapted to provide projection data that has been acquired using a pitch determined such that a same region of the object is imaged by the first part of the detector during a first 360° gantry rotation, the second part of the detector during a following 360° gantry rotation of the detector and by the third part of the detector during a further following 360° gantry rotation of the detector. If the data providing unit is adapted to further provide additional further projection data, it is preferred that the pitch has been determined accordingly. Moreover, the pitch used for acquiring the projection data can also be determined based on a maximum pitch that depends on a diameter of a reconstructed field of view, wherein the pitch is then determined as maximum pitch divided by the number of projection data that should be acquired with a different acquisition spectrum. The number of projection data is, for instance, 2 if first and second projection data are acquired, or 3, when first, second and third projection data are acquired.

In an embodiment, the spectral image generation unit is adapted to reconstruct a first image based on the first projection data and a second image based on the second projection data, and to provide the spectral image by applying an image based spectral separation on the first and second image. An example for an image based spectral separation is given, for instance, in the article "Image-based dual energy CT using optimized precorrection functions: A practical new approach of material decomposition in image domain" by C. Maaß et al., Medical Physics, volume 38, pages 3818-3829 (2009).

Alternatively, the spectral image generation unit can be adapted to use a machine learning approach to generate the spectral image. In such an embodiment, in a training phase, first projection data, second projection data and spectral images generated based on the first and the second projection data are provided to the machine learning system, for instance, to a neural network, to train the machine learning system, wherein after the training phase the machine learning system is configured to generate the spectral image based on provided the first and second projection data.

In an embodiment, the first projection data has been acquired with the first part of the detector and the second projection data has been acquired with the second part of the detector, and the spectral image generation unit is adapted to reconstruct the first and the second image based on the provided projection data comprising the first and the second projection data using an aperture weighted helical reconstruction with shifted aperture weighting functions, wherein for reconstructing the first image a first aperture weighting function is used being only non-zero for projection data acquired in the first part of the detector and wherein for reconstructing the second image a second aperture weighting function is used being only non-zero for projection data acquired in the second part of the detector. A suitable aperture weighted helical reconstruction with shifted aperture weighting functions can be found, for instance, in WO 2018050572.

In an embodiment, the first projection data has been acquired during a scout scan and the second projection data has been acquired during a diagnostic scan, and the spectral image generation unit is adapted to apply a de-noising algorithm to the first image before applying the image based spectral separation. An exemplary de-noising algorithm that can be used with the invention is described in the article "Nonlinear total variation based noise removal algorithms" by L. Rudin et al., Physica D, volume 60, pages 259-268 (1992).

In an embodiment, the first projection data has been acquired during a scout scan and the second projection data has been acquired during a diagnostic scan, and the spectral image generation unit is adapted to register the first and second image with each other before applying the image based spectral separation. The registration between the first and the second image can be performed using any suitable known registration algorithm. One example of a suitable algorithm is described, for instance, in the article "Evaluation of 4D-CT Lung Registration" by S. Kabus et al., MICCAI 2009. Lecture Notes in Computer Science, volume 5761, pages 747-754 (2009).

In an embodiment, the spectral image generation unit is further adapted to segment the first and second image and to base the registration and the image based spectral separation on predetermined segments in the first and second image. The spectral image generation unit can be adapted to segment the first and second image based on any suitable known segmentation algorithm, for instance, based on an algorithm that segments the images in accordance with predetermined image value thresholds. Preferably, if a bone mineral density is to be determined using the spectral image, the segmentation can be based on a bone model of the region of interest to segment the respective bones in the region of interest, wherein then the registration of the first image and the second image is based on the bones segmented in the first image and the second image and wherein further the image based spectral separation is applied to the segmented areas, i.e. to the segmented bones. In case that the accuracy of the segmentation is limited, the spectral information may be generated based on down-sampled first and second images. A down-sampled image is here defined as an image generated from an original image, wherein for the down-sampled image the image data has been interpolated to a voxel size that is greater than the voxel size of the original image. The voxel of a down-sampled image can, for instance, refer to a voxel merged from eight adjacent voxels of the original image.

In a further aspect of the present invention, a method for providing a spectral image is presented, wherein the method comprises providing projection data comprising first projection data and second projection data acquired using a CT system comprising a detector, wherein the first projection data has been acquired using a first acquisition spectrum and the second projection data has been acquired using a second acquisition spectrum, wherein the first projection data has been acquired during a scout scan and the second projection data has been acquired during a diagnostic scan or wherein the first projection data has been acquired by a first part of the detector and the second projection data has been acquired by a second part of the detector, wherein the first part and the second part of the detector acquire projection data with the first acquisition spectrum and the second acquisition spectrum, respectively, due to an anode heel effect, and generating a spectral image based on the provided projection data.

In a further aspect of the present invention, a computer program for providing a spectral image is presented, wherein the computer program comprises program code means for causing the system of claim 1 to carry out the steps of the method as defined in claim 14 when the computer program is run on a computer controlling the system.

It shall be understood that the system of claim 1, the method of claim 14 and the computer program of claim 15 for providing a spectral image of an object have similar and/or identical preferred embodiments, in particular as defined in the dependent claims.

It shall be understood that a preferred embodiment of the present invention can also be any combination of the dependent claims or above embodiments with a respective independent claim.

These and other aspects of the invention will be apparent from and elucidated with reference to the embodiments described hereafter.

DETAILED DESCRIPTION OF EMBODIMENTS

Figure 1:
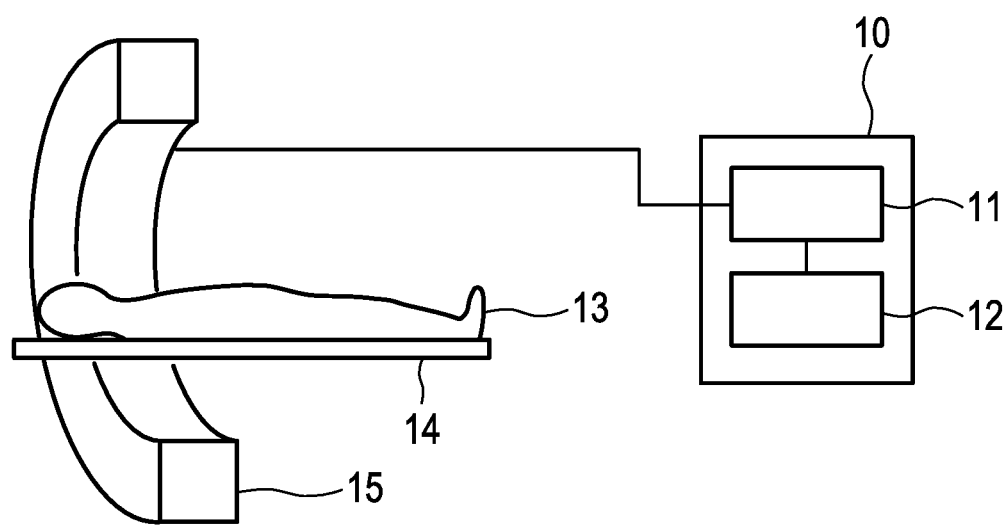
FIG. 1 shows schematically and exemplarily an embodiment of a system for providing a spectral image of an object.

FIG. 1 shows schematically and exemplarily an embodiment of a system for generating a spectral image. In this embodiment, the system 10 is adapted to generate a spectral image of a patient 13 lying on a support means 14, like a patient table. The system 10 comprises a data providing unit 11 for providing projection data of the patient 13 acquired by a CT system 15, wherein the CT system is a conventional CT system, i.e. a non-spectral CT system. Further, the system 10 comprises a spectral image generation unit 12 for generating the spectral image of the patient 13.

In an embodiment, the data providing unit 11 is adapted to provide projection data of the patient 13 comprising first projection data that has been acquired with the CT system 15 with a first acquisition spectrum and second projection data acquired with the CT system 15 with a second acquisition spectrum. Preferably, in this embodiment, the data providing unit 11 is adapted to provide as first projection data projection data that has been acquired during a 3D scout scan of the patient 13. The 3D scout scan can be, for instance, an ultra-low dose 3D scout scan, wherein a radiation source of the CT system 15 is operated during the 3D scout scan with a first energy, i.e. with a first voltage, for providing radiation with a first acquisition spectrum. Further, the data providing unit 11 is in this embodiment adapted to provide as second projection data projection data that has been acquired during a diagnostic scan following the 3D scout scan of the patient 13. The diagnostic scan has been acquired with a radiation source operated with a second energy, i.e. with a second voltage, to acquire second projection data with a second acquisition spectrum. In this embodiment, the spectral image generation unit 12 is adapted to reconstruct, based on the first projection data, a first image and, based on the second projection data, a second image and to generate the spectral image based on the first and second image. This generation of the spectral image will be explained in more detail in the following with respect to FIG. 2.

Figure 2:
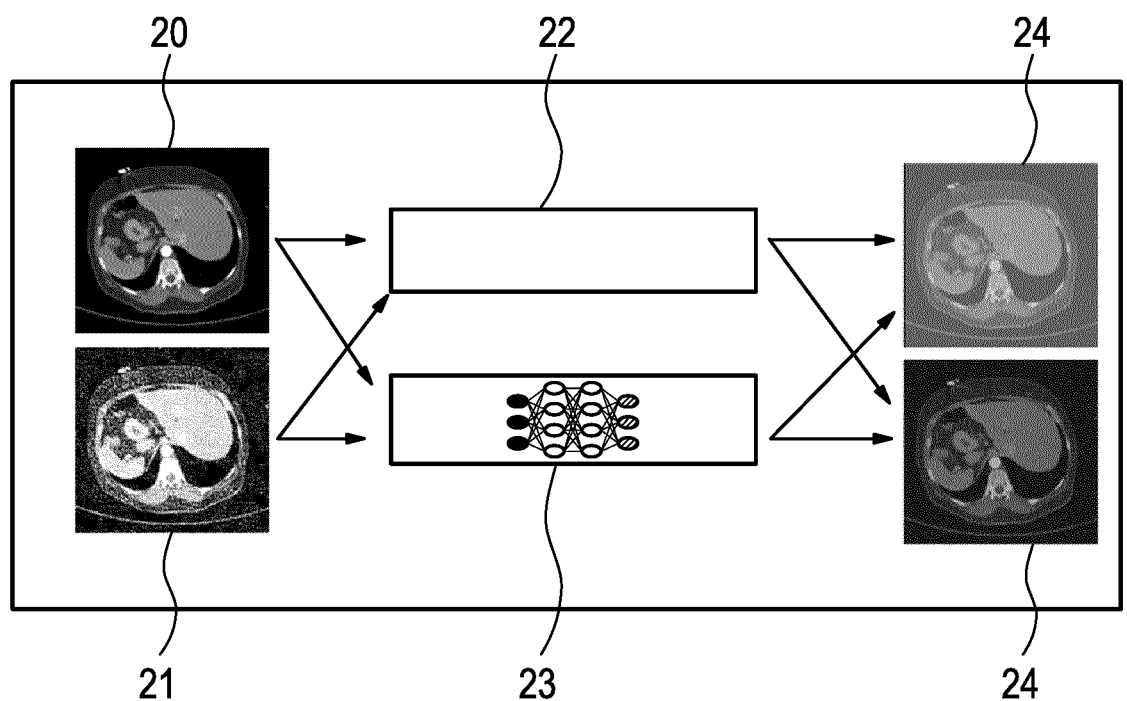
FIG. 2 shows schematically and exemplarily an illustration of an aspect of an embodiment of the system.

In FIG. 2, a first image 21 reconstructed based on the first projection data acquired during the 3D scout scan and a second image 20 reconstructed based on the second projection data acquired during the diagnostic scan are depicted. The spectral image generation unit 12 is adapted to process the first image 21 and the second image 20 to generate spectral images 24. In a first embodiment, the spectral image generation unit 12 is adapted to first register the first image 21 and the second image 20 with each other, to provide a known de-noising algorithm to the first image 21, and to then apply an image based spectral separation algorithm on the first image 21 and the second image 20 to generate the spectral images 24. In FIG. 2, this processing is schematically illustrated by box 22. Additionally or alternatively, the spectral image generation unit 12 can be adapted to process the first image 21 and the second image 20 by using a trained neural network, illustrated in FIG. 2 as a box 23. In this case, the first image 21 and the second image 20 are provided as input to an already trained neural network, wherein the neural network provides the spectral images 24 as output in accordance with its training.

Although in the above embodiment the first projection data was acquired using a first energy for operating the radiation source and the second projection data was acquired using a second energy for operating the radiation source, alternatively or additionally, the first projection data can be acquired by providing a first filter to the radiation emitted by the radiation source and the second projection data can be acquired by providing a second filter to the radiation emitted by the radiation source. In this case, the first filter and the second filter are selected such that the radiation passing the first filter comprises a first acquisition spectrum and the radiation passing the second filter comprises a second acquisition spectrum.

Although in the above embodiment the data providing unit was adapted to provide the first projection data as projection data acquired during a 3D scout scan, the data providing unit can also be adapted to provide the first projection data as projection data acquired during another scan, for instance, an additional scan for providing the first projection data.

Although in the above embodiment the data providing unit was adapted to provide the first projection data having been acquired during a scout scan and the second projection data having been acquired during a diagnostic scan, in another embodiment the data providing unit is adapted to provide first projection data that has been acquired by a first part of the detector and second projection data that has been acquired by a second part of the detector, as will be explained in detail in the following.

In this embodiment, the CT system 15 comprises a multi-row detector, wherein a plurality of detector elements are arranged in consecutive detector element rows. With such a multi-row detector, a plurality of image slices, i.e. projection data corresponding to an image slice in a reconstructed 3D image, can be acquired at the same time. The data providing unit 11 is then adapted to provide as first projection data projection data that has been acquired by detector element rows in the first part of the detector and second projection data that corresponds to projection data that has been acquired by detector element rows in a second part of the detector, as will be explained with reference to FIG. 3 in the following.

In this embodiment, the data providing unit 11 is adapted to provide projection data acquired in a helical scan mode.

In a helical scan mode, a radiation source 32 and a detector 31 can be regarded as moving on a helix 33 around the patient 13. The acquisition scan direction 30 is in this case defined as a direction parallel to the longitudinal, i.e. symmetry, axis of the CT system in which the radiation source 32 moves, i.e. the direction opposing the direction in which the patient table 14 moves during the acquisition of the projection data. A helical scan mode is further defined by a pitch, wherein the pitch is defined as a table distance travelled in one 360° gantry rotation divided by a total thickness of all simultaneously acquired image slices, i.e. the pitch determines the distance between the windings of the helix 13 the radiation source 32 follows with respect to the object. In this embodiment, the pitch is chosen as being smaller than 1, such that a same region of a scanned object is imaged with different parts of the detector at subsequent revolutions, i.e. 360° gantry rotations.

Figure 3:
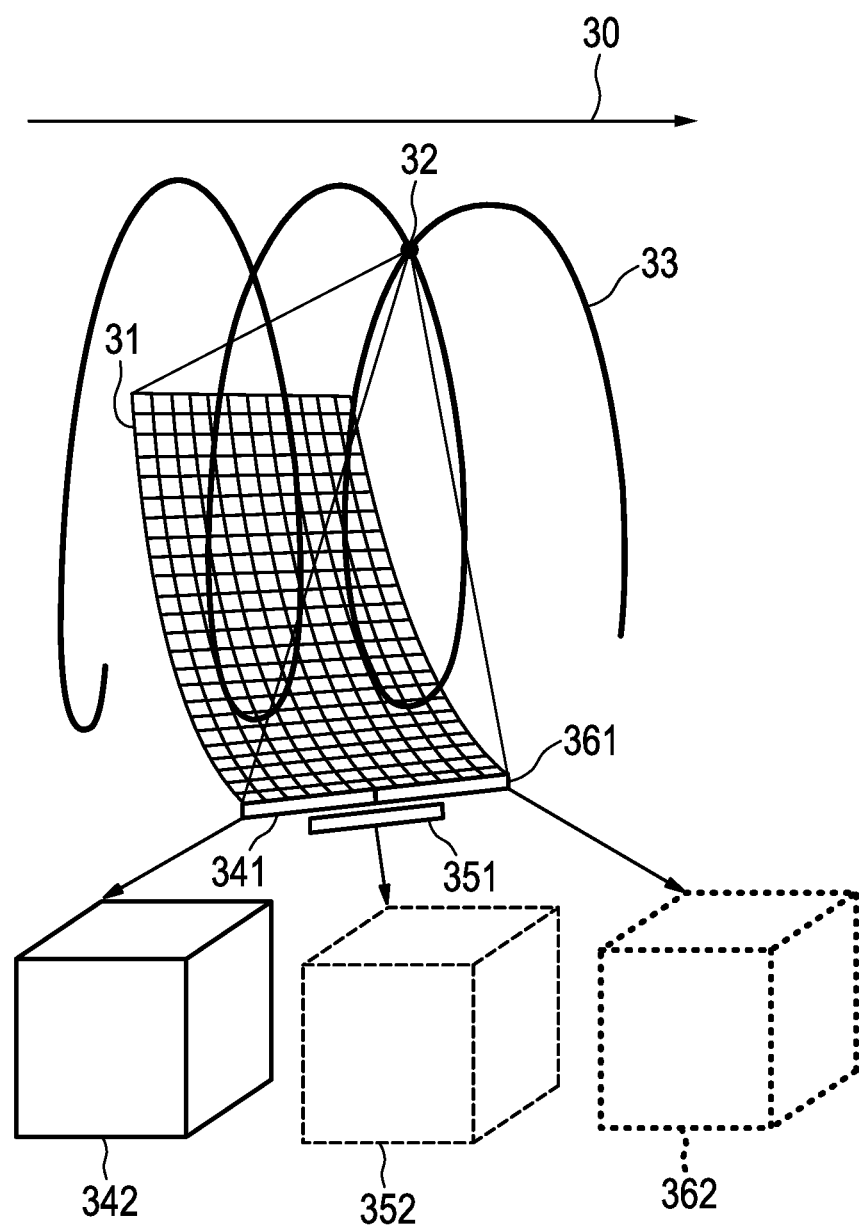
FIG. 3 shows schematically and exemplarily an illustration of an aspect of a further embodiment of the system.

In the embodiment shown in FIG. 3, the projection data acquired by detector 31 comprises first projection data, second projection data and third projection data. The first projection data is acquired with a first part 341 of the detector 31 comprising in this embodiment the last six detector element rows of detector 31 in acquisition direction 30. The second projection data is acquired with the second part 351 of the detector 31, referring in this embodiment to the middle six rows of detector 31, and the third projection data is acquired with a third part 361 of the detector 31, referring in this embodiment to the first six rows of detector 31 in acquisition direction 30. The pitch is in this embodiment chosen such that a same region of the object is imaged by the third part 361 during a gantry revolution, by the second part 351 during a subsequently following gantry revolution, and by the first part 341 during the next subsequently following gantry revolution. Moreover, due to the anode heel effect of the radiation source 32, the first part 341, the second part 351 and the third part 361 of the detector 31 receive radiation comprising a first, a second and a third acquisition spectrum, respectively.

Figure 5:
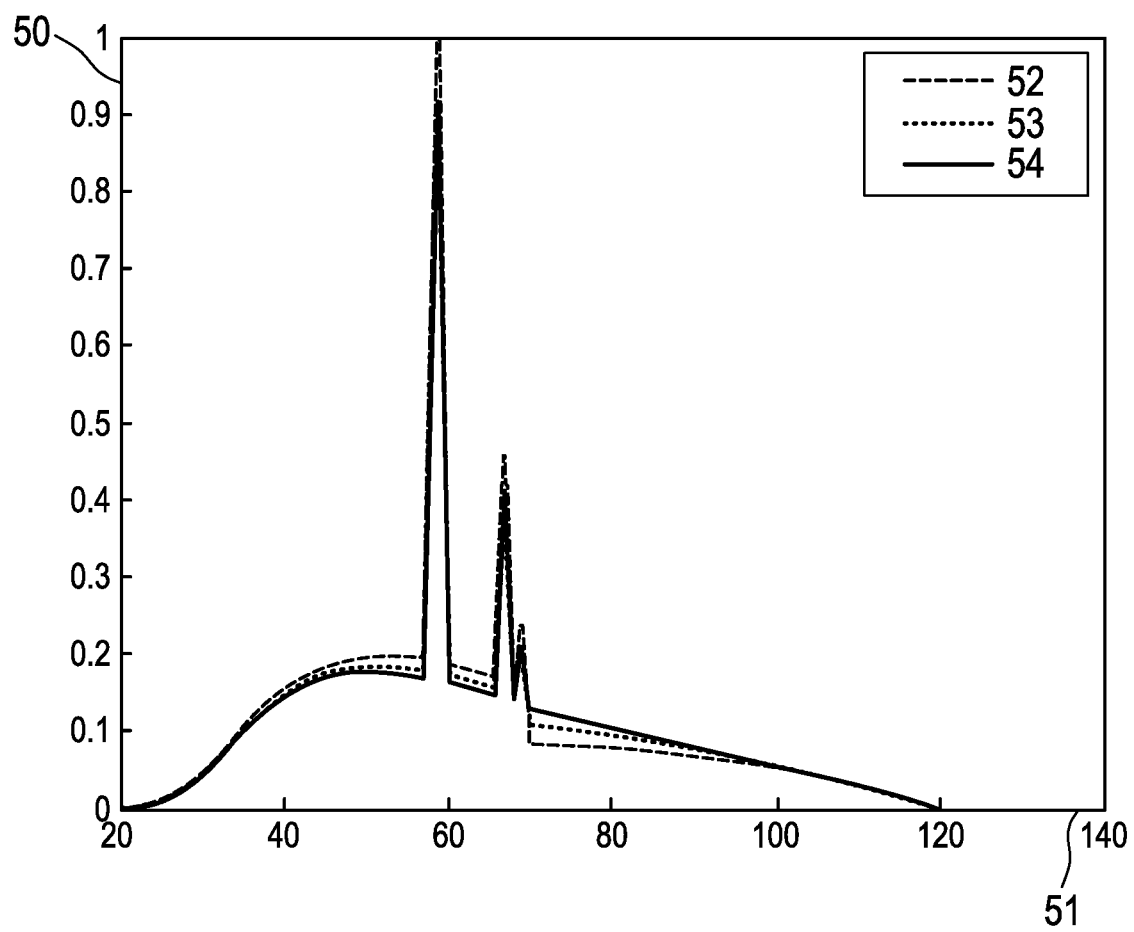
FIGS. 5 and 6 show exemplary spectra for different parts of a detector acquired without the influence of the heel effect and with the influence of the heel effect, respectively.
Figure 6:
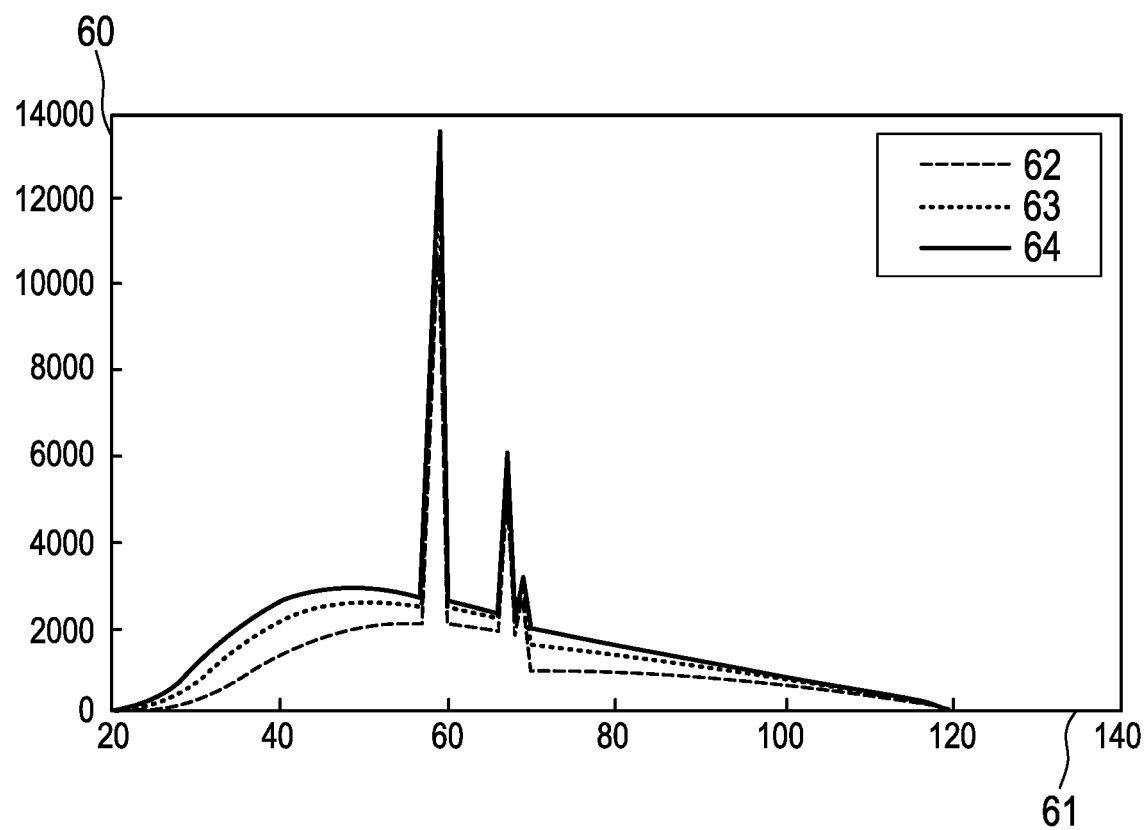

FIGS. 5 and 6 illustrate the respective heel effect for the three parts 341, 351, 361 of the detector for an exemplary CT system. Both figures show a first tube output spectrum 54, 64 corresponding to the first part 341 of the detector 31, a second tube output spectrum 53, 63 corresponding to the second part 351 of the detector 31, and a third tube output spectrum 52, 62 corresponding to the third part 361 of the detector 31, wherein the X-axis 51, 61 reflects the photon energy in keV and the Y-axis 50, 60 depicts the values of the tube output spectra. FIG. 5 shows the first tube output spectrum 54, second tube output spectrum 53 and third tube output spectrum 52, i.e. the first, second and third acquisition spectrum, wherein the radiation emitted by the radiation source has been filtered using an aluminum wedge filter to compensate for the heel effect, as commonly applied during CT image acquisition. As is illustrated, the spectra for the different parts of the detector only show very small differences.

FIG. 6 shows the first tube output spectrum 64, second tube output spectrum 63 and third tube output spectrum 62, i.e. the first, second and third acquisition spectrum, without the application of a heel effect compensation filter. It is illustrated that in this case the spectra for the different parts of the detector are clearly distinguishable and show different spectral characteristics. Accordingly, projection data acquired with these different acquisition spectra provide different spectral information, as can be utilized in an embodiment of the invention.

Accordingly, now referring again to FIG. 3, the image generation unit in this embodiment is adapted to reconstruct a first image 342 from the first projection data acquired with the first part 341 of the detector 31, a second image 352 from the second projection data acquired with the second part 351 of the detector 31 and a third image 362 from the third projection data acquired by the third part 361 of the detector 31. In this embodiment, spectral image generation unit 12 is adapted to reconstruct the first image 342, the second image 352 and the third image 362 from the projection data comprising the first, second and third projection data using an aperture weighted helical reconstruction algorithm with shifted aperture weighting functions. An example for suitably shifting aperture weighting functions is depicted in FIG. 4.

Figure 4:
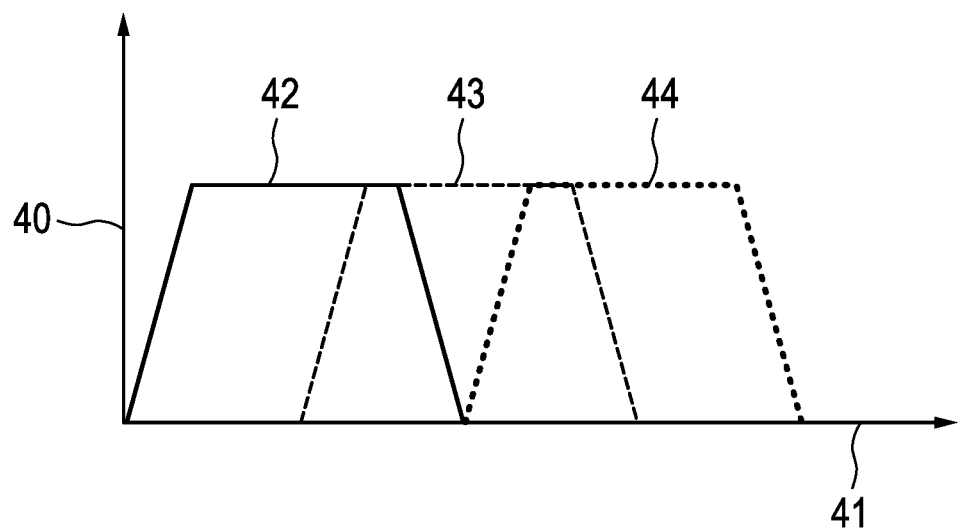
FIG. 4 shows schematically and exemplarily aperture weighting functions suitable to be used with an embodiment of the system.

The graph shown in FIG. 4 comprises an X-axis 41 referring to a respective detector row and a Y-axis 40 referring to values of the weighting function. In this embodiment, the first image 342 is reconstructed with a first weighting function 42, the second image 352 is reconstructed with a second weighting function 43 and the third image 362 is reconstructed with a third weighting function 44. As illustrated in FIG. 4, the first weighting function 42, the second weighting function 43 and the third weighting function 44 only comprise function values substantially greater than zero for detector element rows corresponding to the part of the detector 341, 351, 361 to which the respective image that is to be reconstructed corresponds. Accordingly, the first, second and third image can in this embodiment directly be reconstructed from the projection data comprising the first, second and third projection data and it is not necessary to provide the first, second and third projection data as separate data sets for reconstructing the respective images.

Since the first image 342, the second image 352 and the third image 362 each correspond to projection data acquired with a different acquisition spectrum, spectral information can be derived from the three images. Accordingly, in this embodiment, the spectral image generation unit 12 is adapted to generate the spectral image based on the first image 342, the second image 352 and the third image 362.

Although in the above embodiment the data providing unit is adapted to provide three projection data sets, i.e. the first, second and third projection data, having been acquired by three parts of the detector, in another embodiment the data providing unit can be adapted to provide only two projection data sets or to provide more than three projection data sets, wherein the spectral image generation unit is then adapted to generate the spectral image based on the two or more projection data sets.

Although in the above embodiment the data providing unit is adapted to provide the third image having been acquired by a third part of the detector, in another embodiment the data providing unit can be adapted to provide the third projection data as projection data that has been acquired during a scout scan, in particular during a 3D scout scan. In such an embodiment, the spectral image can be generated based on three projection data sets that have been acquired using three very different acquisition spectra. Thus, even more spectral information can be provided for generating the spectral image.

Although in the above embodiments the spectral image generation unit was adapted to generate the spectral image based on images, for instance, a first image and a second image, reconstructed from the provided projection data, the spectral image generation unit can also be adapted to generate the spectral image directly from the provided projection data, for instance, the first projection data and the second projection data. In such an embodiment, the spectral image generation unit can be, for instance, adapted to use a trained neural network to generate the spectral images from the provided projection data.

Figure 7:
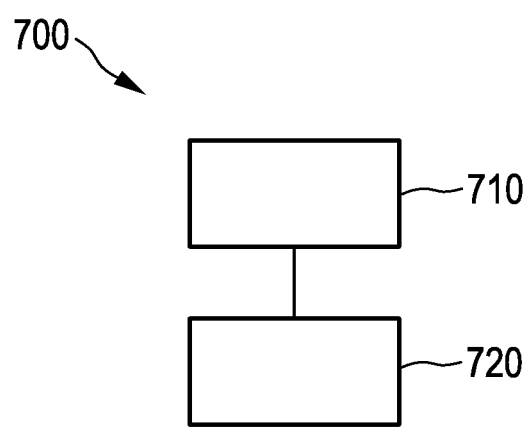
FIG. 7 shows a flow chart exemplarily illustrating an embodiment of a method for providing a spectral image of an object.

FIG. 7 shows a flow chart exemplarily illustrating an embodiment of a method for generating a spectral image of an object. The method 700 comprises a first step 710 of providing the projection data comprising first projection data and second projection data acquired using the CT system 15 in accordance with one of the embodiments described above. Further, the method comprises a second step 720 of generating a spectral image based on the provided projection data, as also disclosed in the above embodiments.

In the present invention, it is proposed to perform a 3D scout scan at a first energy, i.e. by operating the radiation source at a first energy, with a first filtration, i.e. by providing a first filter to the radiation emitted by the radiation source, while performing a diagnostic scan of a planned sub volume of the 3D scout scan at a second energy and a second filtration. This leads to spectral information being available for the same image volume, i.e. the sub volume. In this case, spectral information can be generated on a conventional CT scanner from the 3D scout scan and the diagnostic scan, wherein no additional hardware is required.

The following steps are proposed for an embodiment of this invention. First, a 3D scout scan with a first energy and with a first filtration and a diagnostic scan at a planned sub volume of the 3D scout scan at a second energy and a second filtration are performed. Next, image volumes at identical positions and volume sizes are reconstructed for both scans, i.e. based on the provided projection data of the two scans. In case that motion has occurred, i.e. that the patient has moved, between the 3D scout scan and the diagnostic scan an image based registration can be performed on the image volumes, i.e. on the first image and the second image. Subsequently, an image based spectral separation is applied to the image volumes, i.e. the first image and the second image, to generate photo, Compton, mono-E, or material images, i.e. spectral images. Alternatively to a hand-crafted image based spectral separation algorithm, a machine learning based approach can be used, wherein for instance a neural network is trained for a spectral separation, wherein the neural network can be additionally trained to provide, if necessary, a de-noising to the image volumes, particularly to the first image. In case information on bone mineral density is a primary target of the diagnosis, a model based bone segmentation may be applied to both image volumes and only voxels inside the segmented bones are registered and used for the image based spectral separation. In case that the accuracy of the segmentation is limited, the spectral information may be generated on a down-sampled data set.

In one embodiment of the invention, it is further proposed to make use of the anode heel effect, which modifies the spectrum of an x-ray beam across the detector element rows in z-direction, i.e. in acquisition direction, when using a cone beam CT system. Using a low pitch helical acquisition and a reconstruction with shifted aperture weighting functions, multiple images can be reconstructed which correspond to data acquired with certain detector element rows, i.e. with different parts of the detector. Thereby, image volumes with different spectral information are generated and can be exploited using image based spectral separation.

Although the data might have a low spectral separation yielding a limited signal to noise ratio in the material decomposition, these image volumes can be advantageously used to generate spectral images using known separation approaches or machine learning methods for the spectral separation.

Accordingly, the following steps are proposed for an embodiment of the invention. First, a spectral analysis of the CT scanner, which is used for acquiring the projection data, can be performed via calibration or physical modelling, such that a detector element row dependent spectral characteristic generated by the anode heel effect is determined. Then, projection data can be acquired in a helical scan mode with a low pitch smaller than 1. Subsequently, image volumes at identical position, volume size, and resolution can be reconstructed using aperture weighted helical reconstruction with shifted aperture weighting functions. Since redundant data are acquired due to the low pitch, the aperture weighting function can be chosen in a way that it is only significantly non-zero in a certain area of the detector. Depending on the pitch, two or even more image volumes can be reconstructed using different data and yielding different effective acquisition spectra. Accordingly, an image based spectral separation based on the multiple image volumes reconstructed in the previous step with different spectral characteristics can be performed. Moreover, while multiple images with different spectral characteristics can be generated using this method, a conventional CT image is also always available when all data is taken into account for the reconstruction. In further embodiments, an additional beam filter may be used to increase the heel effect induced modification of the spectrum.

Other variations to the disclosed embodiments can be understood and effected by those skilled in the art and practicing the planned invention from the study of the drawings, the disclosure and the appendant claims.

In the claims, the word "comprising" does not exclude other elements or steps, and the indefinite article "a" or "an" does not exclude a plurality.

A single unit or device may fulfill the functions of several items to be cited in the claims. The mere fact that certain measures are recited in mutually different dependent claims does not indicate that a combination of these measures cannot be used to advantage.

Procedures like the generating of the spectral image or the providing of the projection data performed by one or several units or devices can be performed by any other number of units or devices. The procedures and/or the operations of the system can be implemented as program code means of a computer program and/or as dedicated hardware. A computer program may be stored/distributed in a suitable medium, such as an optical storage medium or a solid state storage medium, supplied together with or as part of other hardware, but might also be distributed in other forms, such as via the internet or other wired or wireless telecommunication systems.

Any reference signs in the claims should not be construed as limiting the scope.

The invention refers to a system for providing a spectral image using a conventional CT system. The system comprises a data providing unit for providing first projection data and second projection data, wherein the first and second projection data have been acquired using different acquisition spectra, wherein the first projection data has been acquired during a scout scan and the second projection data has been acquired during a diagnostic scan, or wherein the first and second projection data have been acquired by a first and second part of the detector, respectively. The first and second part of the detector acquire projection data with different acquisition spectra. A spectral image generation unit generates a spectral image based on the projection data. With this system a spectral image can be provided using a conventional CT system with a decreased acquisition time.

The invention claimed is:

1. A system for providing a spectral image, wherein the system comprises:
    a data provider for providing projection data comprising first projection data and second projection data acquired using a computed tomography (CT) system comprising a detector, wherein the first projection data has been acquired using a first acquisition spectrum and the second projection data has been acquired using a second acquisition spectrum, wherein the first projection data has been acquired by a first part of the detector and the second projection data has been acquired by a second part of the detector, wherein the first part and the second part of the detector acquire projection data with the first acquisition spectrum and the second acquisition spectrum, respectively, due to an anode heel effect; and
    a spectral image generator for generating a spectral image based on the provided projection data.

2. The system according to claim 1, wherein the CT system comprises a radiation source and wherein the first projection data has been acquired by providing the radiation source with a first filter for filtering the radiation of the radiation source, and the second projection data has been acquired by providing the radiation source with a second filter for filtering the radiation of the radiation source.

3. The system according to claim 1, wherein the data provider is further configured to provide spectral characteristics indicative of the characteristics of the first acquisition spectrum and of the second acquisition spectrum, wherein the spectral generator is configured to generate the at least one spectral image further based on the provided spectral characteristics.

4. The system according to claim 1, wherein the first projection data acquired with the first part of the detector and the second projection data acquired with the second part of the detector have been acquired during the same acquisition scan, wherein the acquisition scan has been performed in a helical scan mode with a pitch smaller than 1.

5. The system according to claim 4, wherein the pitch used for the acquisition scan depends on the extent of the first and/or second part of the detector in the acquisition scan direction.

6. The system according to claim 1, wherein the CT system comprises a radiation source and wherein the first projection data acquired with the first part of the detector and the second projection data acquired with the second part of the detector have been acquired using a spectral filter that increases a spectral difference of the first acquisition spectrum and the second acquisition spectrum caused by the anode heel effect.

7. The system according to claim 1, wherein the spectral image generator is configured to reconstruct a first image based on the first projection data and a second image based on the second projection data and to provide the spectral image by applying an image based spectral separation on the first and second image.

8. The system according to claim 7, wherein the first projection data has been acquired with the first part of the detector and the second projection data has been acquired with the second part of the detector, and wherein the spectral image generator is configured to reconstruct the first and the second image based on the provided projection data comprising the first and the second projection data using an aperture weighted helical reconstruction with shifted aperture weighting functions, wherein for reconstructing the first image a first aperture weighting function is used being only non-zero for projection data acquired in the first part of the detector, and wherein for reconstructing the second image a second aperture weighting function is used being only non-zero for projection data acquired in the second part of the detector.

9. The system according to claim 7, wherein the first projection data has been acquired during a scout scan and the second projection data has been acquired during a diagnostic scan, and wherein the spectral image generator is configured to apply a de-noising algorithm to the first image before applying the image based spectral separation.

10. The system according to claim 7, wherein the first projection data has been acquired during a scout scan and the second projection data has been acquired during a diagnostic scan, and wherein the spectral image generator is configured to register the first and second image with each other before applying the image based spectral separation.

11. The system according to claim 10, wherein the spectral image generator is further configured to segment the first and second image and to base the registration and the image based spectral separation on predetermined segments in the first and second image.

12. A method for providing a spectral image, comprising:
    providing projection data comprising first projection data and second projection data acquired using a CT system comprising a detector, wherein the first projection data has been acquired using a first acquisition spectrum and the second projection data has been acquired using a second acquisition spectrum, wherein the first projection data has been acquired by a first part of the detector and the second projection data has been acquired by a second part of the detector, wherein the first part and the second part of the detector acquire projection data with the first acquisition spectrum and the second acquisition spectrum, respectively, due to an anode heel effect; and
    generating a spectral image based on the provided projection data.

13. A non-transitory computer-readable medium for storing executable instructions, which cause a method to be performed to provide a spectral image, the method comprising:
    providing projection data comprising first projection data and second projection data acquired using a CT system comprising a detector, wherein the first projection data has been acquired using a first acquisition spectrum and the second projection data has been acquired using a second acquisition spectrum, wherein the first projection data has been acquired by a first part of the detector and the second projection data has been acquired by a second part of the detector, wherein the first part and the second part of the detector acquire projection data with the first acquisition spectrum and the second acquisition spectrum, respectively, due to an anode heel effect; and
    generating a spectral image based on the provided projection data.

* * * * *